United States Patent [19]
Harmer et al.

[11] Patent Number: 6,034,290
[45] Date of Patent: Mar. 7, 2000

[54] POROUS MICROCOMPOSITE OF METAL CATION EXCHANGED PERFLUORINATED ION-EXCHANGE POLYMER AND NETWORK OF METAL OXIDE, SILICA, OR METAL OXIDE AND SILICA

[75] Inventors: Mark Andrew Harmer; Qun Sun, both of Wilmington, Del.

[73] Assignee: E. I. du Pont de Nemours and Company, Wilmington, Del.

[21] Appl. No.: 09/277,094

[22] Filed: Mar. 26, 1999

Related U.S. Application Data

[60] Division of application No. 08/683,998, Jul. 19, 1996, Pat. No. 5,916,837, which is a continuation-in-part of application No. 08/574,751, Dec. 19, 1995, Pat. No. 5,824,622, which is a continuation-in-part of application No. 08/362,063, Dec. 22, 1994, abandoned, which is a continuation-in-part of application No. 08/180,250, Jan. 12, 1994, abandoned.

[30] Foreign Application Priority Data

| Jan. 10, 1995 | [WO] | WIPO | PCTUS9500012 |
| Dec. 20, 1995 | [WO] | WIPO | PCTUS9516566 |

[51] Int. Cl.[7] .......................... C07C 17/00; C07C 19/00; C07C 21/00; C07C 21/02
[52] U.S. Cl. .......................................................... 570/236
[58] Field of Search .................................................. 570/236

[56] References Cited

U.S. PATENT DOCUMENTS

| | | | |
|---|---|---|---|
| 3,151,179 | 9/1964 | Kennedy et al. | 260/683.2 |
| 3,506,635 | 4/1970 | Anderson | 260/88.3 |
| 4,038,213 | 7/1977 | McClure et al. | 252/430 |
| 4,041,090 | 8/1977 | McClure | 260/671 R |
| 4,056,578 | 11/1977 | McClure et al. | 260/683.47 |
| 4,065,515 | 12/1977 | McClure et al. | 260/683.68 |
| 4,414,409 | 11/1983 | Waller | 560/233 |
| 4,433,082 | 2/1984 | Grot | 524/755 |
| 4,446,329 | 5/1984 | Waller | 585/458 |
| 4,661,411 | 4/1987 | Martin et al. | 428/421 |
| 4,791,081 | 12/1988 | Childress et al. | 502/62 |
| 4,983,566 | 1/1991 | Wieserman et al. | 502/401 |
| 4,994,429 | 2/1991 | Wieserman et al. | 502/401 |
| 5,086,085 | 2/1992 | Pekala | 521/187 |
| 5,094,995 | 3/1992 | Butt et al. | 502/402 |
| 5,105,047 | 4/1992 | Waller | 585/515 |
| 5,124,299 | 6/1992 | Waller | 502/159 |
| 5,126,210 | 6/1992 | Wieserman et al. | 428/469 |
| 5,252,654 | 10/1993 | David et al. | 524/414 |
| 5,338,430 | 8/1994 | Parsonage et al. | 204/412 |
| 5,430,212 | 7/1995 | Butt et al. | 585/526 |
| 5,472,926 | 12/1995 | Gubitosa et al. | 502/337 |
| 5,824,622 | 10/1998 | Harmer et al. | 502/407 |

FOREIGN PATENT DOCUMENTS

| | | |
|---|---|---|
| 0 288 295 | 10/1988 | European Pat. Off. . |
| 0324080 | 7/1989 | European Pat. Off. . |
| 0 338 309 | 10/1989 | European Pat. Off. . |
| 0367408 | 5/1990 | European Pat. Off. . |
| 0503688 | 9/1992 | European Pat. Off. . |
| 1.248.426 | 12/1960 | France . |
| 1.512.817 | 2/1968 | France ................................. 570/236 |
| 1 287 063 | 1/1969 | Germany .............................. 570/236 |
| 1 802 385 | 11/1969 | Germany .............................. 570/236 |
| 41-419 | 1/1966 | Japan .................................... 570/236 |
| 42-3613 | 2/1967 | Japan .................................... 570/236 |
| 42-25052 | 11/1967 | Japan .................................... 570/236 |
| 46-8281 | 3/1971 | Japan .................................... 570/236 |

OTHER PUBLICATIONS

Abruna, H.D., *Coordination Chemistry Review*, 86, 135–189, 1988.
Waller, F.J., *Catal. Rev.–Sci. Eng.*, 1–12, 1986.
Olah, G. A. et al., Synthesis, 513–531, 1986.
Weaver, J.D. et al., *Catalysis Today*, 14, 195–210, 1992.
Mauritz, K.A. et al., Multiphase Polymers: Blends and Ionomers, American Chemical Society, 401–417, Chapter 16, 1989.
Waller, F.J. et al. Chemtech, 438–441 (Jul. 1987).
Waller, F.J., In *Polymeric Reagents and Catalysts*, Ford, W.T. (Ed.), Chap. 3, ACS Symposium Series 308, ACS Washington, DC (1986).
Martin, C.R. et al., Anal. Chem. 54, 1639–1641 (1982).
Mauritz, K.A. et al., *Polym. Mater. Sci. Eng.*, 58, 1079–1082, 1988.

*Primary Examiner*—Mark L. Bell
*Assistant Examiner*—J. Pasterczyk

[57] ABSTRACT

Porous microcomposites comprising a perfluorinated ion-exchange polymer (PFIEP) containing pendant metal cation exchanged sulfonate groups, metal cation exchanged carboxylate groups, or metal cation exchanged sulfonate and carboxylate groups, wherein the metal cation may be ligand coordinated, and optionally pendant sulfonic acid groups, carboxylic acid groups, or sulfonic acid and carboxylic acid groups, the PFIEP being entrapped within and highly dispersed throughout a network of metal oxide, a network of silica or a network of metal oxide and silica can be prepared from PFIEP and one or more precursors selected from the group consisting of a metal oxide precursor, a silica precursor, and a metal oxide and silica precursor using an in situ process. Preferred metal cations are Cr, Sn, Al, Fe, Os, Co, Zn, Hg, Li, Na, Cu, Pd or Ru. Such microcomposites have a first set of pores having a pore size diameter ranging from about 0.5 nm to about 75 nm and may further comprise a second set of pores having a diameter ranging from about 75 nm to about 1000 nm. These microcomposites possess high surface area and exhibit high catalytic activity. The catalyst is used to isomerize 1,4-dichloro-2-butene to 3,4-dichloro-1-butene, a precursor to neoprone.

3 Claims, No Drawings

POROUS MICROCOMPOSITE OF METAL CATION EXCHANGED PERFLUORINATED ION-EXCHANGE POLYMER AND NETWORK OF METAL OXIDE, SILICA, OR METAL OXIDE AND SILICA

This application is a division of application Ser. No. 08/683,998 filed Jul. 19, 1996 now U.S. Pat. No. 5,916,837, which is a continuation-in-part of application Ser. No. 08/574,751 filed Dec. 19, 1995, which issued as U.S. Pat. No. 5,824,622 on Oct. 20, 1998, which is a continuation-in-part of application Ser. No. 08/362,063 filed Dec. 22, 1994, now abandoned, which is a continuation-in-part of application Ser. No. 08/180,250 filed Jan. 12, 1994, now abandoned.

FIELD OF THE INVENTION

This invention relates to a porous microcomposite comprising a perfluorinated ion-exchange polymer (PFIEP) and a metal oxide network.

TECHNICAL BACKGROUND

The catalytic utility of perfluorinated ion-exchange polymers (PFIEP) containing pendant sulfonic acid groups, supported and unsupported, has been broadly reviewed: G. A. Olah et al., Synthesis, 513–531(1986) and F. J. Waller, Catal. Rev.-Sci. Eng., 1–12 (1986). Although these catalysts have been utilized in a variety of applications, there are certain reactions for which they have demonstrated poor or no activity. For example, the attempted use of such catalysts in the isomerization of 1,4-dichlorobutene-2 to 3,4-dichlorobutene-1 has shown little activity.

An existing process for converting 1,4-dichlorobutene-2 to 3,4-dichlorobutene-1 takes place in a homogeneous liquid phase in a boiling reactor using tetraalkylammonium chloride as a catalyst. 3,4-dichlorobutene-1 is the desired intermediate in the manufacture of chloroprene which is then polymerized to make Neoprene. High boiling point products are one undesirable disadvantage to this isomerization process.

It is an object of the present invention to provide a catalyst for use in the isomerization of 1,4-dichlorobutene-2 to 3,4-dichlorobutene-1 without the undesirable by-products of existing this process.

Perfluorinated ion-exchange polymers and perfluorinated ion-exchange polymers modified with cationic complexes have also been used extensively in the area of surface modified electrodes. See for example "Coordination Chemistry in Two Dimensions: Chemically Modified Electrodes" by H. D. Abruna, Coordination Chemistry Review, 86(1988) 135–189. Such perfluorinated ion exchange polymers have been applied to electrodes and used for electrocatalysis. One problem that is encountered with these materials is their small apparent diffusion coefficients which have been ascribed to various effects including poor swelling. Another object of the present invention is to provide a catalyst which will provide rapid diffusion in these types of applications.

SUMMARY OF THE INVENTION

This invention provides a porous microcomposite comprising a perfluorinated ion-exchange polymer containing pendant metal cation exchanged sulfonate and/or metal cation exchanged carboxylate groups, wherein the metal cation may be ligand coordinated, and optionally pendant sulfonic acid and/or carboxylic acid groups, entrapped within and highly dispersed throughout a network of metal oxide, wherein the weight percentage of the perfluorinated ion-exchange polymer in the microcomposite is from about 0.1 to 90 percent, wherein the size of the pores in the microcomposite is about 0.5 nm to about 75 nm, and wherein the microcomposite optionally further comprises pores having a size in the range of about 75 nm to about 1000 nm.

This invention further provides a process for the preparation of a porous microcomposite comprising a perfluorinated ion-exchange polymer containing pendant metal cation exchanged sulfonate and/or metal cation exchanged carboxylate groups, wherein the metal cation may be ligand coordinated, and optionally pendant sulfonic acid and/or carboxylic acid groups, entrapped within and highly dispersed throughout a network of metal oxide, wherein the weight percentage of the perfluorinated ion-exchange polymer in the microcomposite is from about 0.1 to 90 percent, said process comprising the steps of:

a. mixing a solution comprising a perfluorinated ion-exchange polymer containing metal cation exchanged sulfonate and/or metal cation exchanged carboxylate groups, wherein the metal cation may be ligand coordinated, and optionally pendant sulfonic acid and/or carboxylic acid groups, at least one metal oxide precursor and a common solvent;

b. initiating gelation;

c. allowing sufficient time for gelation and optional aging of the mixture; and d. removing the solvent to yield the porous microcomposite, wherein the size of the pores in the microcomposite is about 0.5 nm to about 75 nm.

This invention also provides a process for the preparation of a porous microcomposite comprising a perfluorinated ion-exchange polymer containing pendant metal cation exchanged sulfonate and/or metal cation exchanged carboxylate groups, where the metal cation may be ligand coordinated, and optionally pendant sulfonic acid and/or carboxylic acid groups, entrapped within and highly dispersed throughout a network of metal oxide, wherein the weight percentage of the perfluorinated ion-exchange polymer in the microcomposite is from about 0.1 to 90 percent, wherein the size of the pores in the microcomposite is about 0.5 nm to about 75 nm, and wherein the microcomposite optionally further comprises pores having a size in the range of about 75 nm to about 1000 nm; said process comprising the steps of:

a. contacting a porous microcomposite comprising a perfluorinated ion-exchange polymer containing pendant sulfonic acid and/or carboxylic acid groups entrapped within and highly dispersed throughout a network of metal oxide, wherein the weight percentage of the perfluorinated ion-exchange polymer in the microcomposite is from about 0.1 to 90 percent, wherein the size of the pores in the microcomposite is about 0.5 nm to about 75 nm, and wherein the microcomposite optionally further comprises pores having a size in the range of about 75 nm to about 1000 nm, with an aqueous solution comprising at least one metal salt or a salt of a ligand coordinated metal; and b. removing the solvent to yield the porous microcomposite.

The present invention also provides a process for the isomerization of 1,4-dichlorobutene-2 to 3,4-dichlorobutene-1 comprising:

contacting 1,4-dichlorobutene-2 with a catalytic amount of a porous microcomposite which comprises a perfluorinated ion-exchange polymer containing pendant metal cation exchanged sulfonate and/or metal cation exchanged carboxylate groups, wherein the metal cation may be ligand coordinated, and optionally pendant sulfonic acid and/or carboxylic acid groups, entrapped within and highly dispersed throughout a network of metal oxide, wherein the weight percentage of the perfluorinated ion-exchange polymer in the microcomposite is from about 0.1 to 90 percent, wherein the size of the pores in the microcomposite is about 0.5 nm to about 75 nm, and wherein the microcomposite optionally further comprises pores having a size in the range of about 75 nm to about 1000 nm, in a common solvent, or neat without solvent, under an inert atmosphere at a temperature ranging from about 80° C. to about 180° C.; and recovering the 3,4-dichlorobutene-1.

The present invention further provides an electrode coating, comprising a porous microcomposite which comprises a perfluorinated ion-exchange polymer containing pendant metal cation exchanged sulfonate and/or metal cation exchanged carboxylate groups, wherein the metal cation may be ligand coordinated, or pendant electrochemically active organic cation sulfonate and/or electrochemically active organic cation carboxylate groups, and optionally pendant sulfonic acid and/or carboxylic acid groups, entrapped within and highly dispersed throughout a network of metal oxide, wherein the weight percentage of perfluorinated ion-exchange polymer in the microcomposite is from about 0.1 to about 90 percent, wherein the size of the pores in the microcomposite is about 0.5 nm to about 75 nm, and wherein the microcomposite optionally further comprises pores having a size in the range of about 75 nm to about 1000 nm.

The present invention also provides an electrochromic material, comprising: a porous microcomposite which comprises a perfluorinated ion-exchange polymer containing pendant metal cation exchanged sulfonate and/or metal cation exchanged carboxylate groups, wherein the metal cation may be ligand coordinated, or pendant electrochemically active organic cation sulfonate and/or electrochemically active organic cation carboxylate groups, and optionally pendant sulfonic acid and/or carboxylic acid groups, entrapped within and highly dispersed throughout a network of metal oxide, wherein the weight percentage of perfluorinated ion-exchange polymer in the microcomposite is from about 0.1 to about 90 percent, wherein the size of the pores in the microcomposite is about 0.5 nm to about 75 nm, and wherein the microcomposite optionally further comprises pores having a size in the range of about 75 nm to about 1000 nm.

DETAILED DESCRIPTION OF THE INVENTION

The present invention provides a porous microcomposite comprising a perfluorinated ion-exchange polymer containing pendant metal cation exchanged sulfonate and/or metal cation exchanged carboxylate groups, wherein the metal cation may be ligand coordinated, and optionally pendant sulfonic acid and/or carboxylic acid groups, entrapped within and highly dispersed throughout a network of metal oxide, wherein the weight percentage of perfluorinated ion-exchange polymer in the microcomposite is from about 0.1 to 90 percent, preferably from about 5 to about 80 percent, most preferably about 5 to about 25 percent, wherein the size of the pores in the microcomposite is about 0.5 nm to about 75 nm, and wherein the microcomposite optionally further comprises pores having a size in the range of about 75 nm to about 1000 nm.

The composition of the present invention exists as a particulate solid which is porous and glass-like in nature, typically 0.1–4 mm in size and structurally hard, similar to dried silica gels. The porous nature of the microcomposite is evident from the high surface areas measured for these glass-like pieces. Macroporosity (pore sizes of about 75 nm to about 1000 nm) can be introduced into the microcomposite by methods described herein resulting in a microcomposite having both increased surface area from the micropores and mesopores (about 0.5 nm to about 75 nm in size) and enhanced accessibility resulting from the macropores (about 75 to about 1000 nm in size). Microcomposites of the present invention can also be used in pulverized form.

Perfluorinated ion-exchange polymers (PFIEP) containing pendant sulfonic acid, carboxylic acid, or sulfonic acid and carboxylic acid groups which can be used in the preparation of microcomposites of the present invention are well known compounds. See, for example, Waller et al., Chemtech, July, 1987, pp. 438–441, and references therein, and U.S. Pat. No. 5,094,995, incorporated herein by reference. PFIEP containing pendant carboxylic acid groups have been described in U.S. Pat. No. 3,506,635, which is also incorporated by reference herein. Polymers discussed by J. D. Weaver et al., in Catalysis Today, 14 (1992) 195–210, are also useful in the present invention. Polymers that are suitable for use in the present invention have structures that include a substantially fluorinated carbon chain that may have attached to it side chains that are substantially fluorinated. In addition, these polymers contain sulfonic acid groups or derivatives of sulfonic acid groups, carboxylic acid groups or derivatives of carboxylic acid groups and/or mixtures of these groups. For example, copolymers of a first fluorinated vinyl monomer and a second fluorinated vinyl monomer having a pendant cation exchange group or a pendant cation exchange group precursor can be used, e.g., sulfonyl fluoride groups ($SO_2F$) which can be subsequently hydrolyzed to sulfonic acid groups. Possible first monomers include tetrafluoroethylene (TFE), hexafluoropropylene, vinyl fluoride, vinylidine fluoride, trifluoroethylene, chlorotrifluoroethylene, perfluoro (alkyl vinyl ether), and mixtures thereof. Possible second monomers include a variety of fluorinated vinyl ethers with pendant cation exchange groups or precursor groups. Preferably, the polymer contains a sufficient number of pendant groups to give an equivalent weight of from about 500 to 20,000, and most preferably from 800 to 2000. Representative of the perfluorinated polymers for use in the present invention are "NAFION®" PFIEP (a family of polymers for use in the manufacture of industrial chemicals, commercially available from E. I. du Pont de Nemours and Company), and polymers, or derivatives of polymers, disclosed in U.S. Pat. Nos. 3,282,875; 4,329,435; 4,330,654; 4,358,545; 4,417,969; 4,610,762; 4,433,082; and 5,094,995. More preferably the polymer comprises a perfluorocarbon backbone and a pendant group represented by the formula $-OCF_2CF(CF_3)OCF_2CF_2SO_3X$, wherein X is $H^+$, an alkali metal cation or $NH_4^+$. Polymers of this type are disclosed in U.S. Pat. No. 3,282,875.

Typically, suitable perfluorinated polymers are derived from sulfonyl group-containing polymers having a fluorinated hydrocarbon backbone chain to which are attached the functional groups or pendant side chains which in turn carry the functional groups. Fluorocarbosulfonic acid catalysts polymers useful in preparing the microcomposites of the present invention have been made by Dow Chemical and are described in Catalysis Today, 14 (1992) 195–210. Other perfluorinated polymer sulfonic acid catalysts are described in Synthesis, G. I. Olah, P. S. Iyer, G. K. Surya Prakash, 513–531 (1986).

Other classes of ion-exchange polymers useful in preparing the microcomposite of the present invention comprise 1) a partially cation-exchanged polymer, 2) a completely cation-exchanged polymer, and 3) a cation-exchanged polymer where the metal cation is coordinated to another ligand (see U.S. Pat. No. 4,414,409; Waller, F. J. In Polymeric Reagents and Catalysts; Ford, W. T., Ed..; ACS Symposium Series 308; American Chemical Society; Washington. D.C., 1986, Chapter 3; and Waller (Catal. Rev. Sci. Eng. 28(1), 1–12 (1986)). These types of polymers can be used directly in forming the present microcomposite, or a fully acidified microcomposite prepared from these or other classes of PFIEP can be converted to a metal cation exchanged microcomposite. Preferred PFIEP suitable for use in the present invention comprise those containing pendant metal cation exchanged sulfonate groups, wherein the metal cation may be ligand coordinated, and optionally further containing pendant sulfonic acid groups. Most preferred is a sulfonated "NAFION®" PFIEP with such pendant groups.

In the present microcomposite, the PFIEP contains pendant metal cation exchanged sulfonate and/or pendant metal cation exchanged carboxylate groups. The metal cations are bound to anionically charged sulfonate and/or carboxylate groups through an exchange with, for example $H^+$. Preferably, the metal cations of the PFIEP pendant groups of the present microcomposite are selected from the group consisting of Cr, Sn, Al, Fe, Os, Co, Zn, Hg, Li, Na, Cu, Pd, and Ru; most preferred metal cations are Cu and Pd. Representative and preferred examples of ligand coordinated metals on PFIEP pendant groups are $(Ru(bipyridyl)_3)^{2+}$, $(Fe(bipyridyl)_3)^{2+}$, $(Os(bipyridyl)_3)^{2+}$, $[Ru(NH_3)_6]^{3+}$, $(Co(bipyridyl)_3)^{2+}$ and the like.

Perflourinated ion-exchange polymers are used within the context of the invention in solution form. It is possible to dissolve the polymer by heating it with an aqueous alcohol to about 240° C. or higher for several hours in a high pressure autoclave (see U.S. Pat. No. 4,433,082 or Martin et al., Anal. Chem., Vol. 54, pp 1639–1641 (1982). Other solvents and mixtures may also be effective in dissolving the polymer.

Ordinarily, for each part by weight of polymer employed to be dissolved, from as little as about 4 or 5 parts by weight up to about 100 parts by weight, preferably 20–50 parts by weight, of the solvent mixture are employed. In the preparation of the dissolved polymer, there is an interaction between the equivalent weight of the polymer employed, the temperature of the process, and the amount and nature of the solvent mixture employed. For higher equivalent weight polymers, the temperature employed is ordinarily higher and the amount of liquid mixture employed is usually greater.

The resulting mixture can be used directly and may be filtered through fine filters (e.g., 4–5.5 micrometers) to obtain clear, though perhaps slightly colored solutions. The mixtures obtained by this process can be further modified by removing a portion of the water, alcohols and volatile organic by-products by distillation.

Commercially available solutions of perfluorinated ion-exchange polymers can also be used in the preparation of the microcomposite of the present invention (e.g., a 5 wt % solution of a perfluorinated ion-exchange powder in a mixture of lower aliphatic alcohols and water, Cat. No. 27,470–4, Aldrich Chemical Company, Inc., 940 West Saint Paul Avenue, Milwaukee, Wis. 53233).

The PFIEP of the present microcomposite preferably contains pendant metal cation exchanged sulfonate groups, and optionally pendant sulfonic acid groups, wherein the metal cation may be ligand coordinated, and wherein the metal cation exchanged sulfonate groups constitute 1 to 100% of the total sulfonate plus sulfonic acid groups present; or the PFIEP of the present microcomposite preferably contains pendant metal cation exchanged carboxylate groups, and optionally pendant carboxylic acid groups, wherein the metal cation may be ligand coordinated, and wherein the metal cation exchanged carboxylate groups constitute 1 to 100% of the total carboxylate plus carboxylic acid groups present.

"Metal oxide" signifies metallic or semimetallic oxide compounds, including, for example, alumina, silica, titania, germania, zirconia, alumino-silicates, zirconyl-silicates, chromic oxides, germanium oxides, copper oxides, molybdenum oxides, tantalum oxides, zinc oxides, yttrium oxides, vanadium oxides, and iron oxides. Preferably, the network of metal oxide of the present microcomposite is selected from the group consisting of: silica, alumina, titania, germania, zirconia, alumino-silicate, zirconyl-silicate, chromic oxide and iron oxide. Silica is the most preferred metal oxide. The term "metal oxide precursor" refers to the form of the metal oxide which is originally added in the sol-gel process to finally yield a metal oxide in the final microcomposite. In the case of silica, for example, it is well known that a range of silicon alkoxides can be hydrolyzed and condensed to form a silica network. Such precursors as tetramethoxysilane, tetraethoxysilane, tetrapropoxysilane, tetrabutoxysilane, and any compounds under the class of metal alkoxides which in the case of silicon is represented by $Si(OR)_4$, where R includes methyl, ethyl, n-propyl, iso-propyl, n-butyl, sec-butyl, iso-butyl, tert-butyl or where R is a range of organic groups, such as alkyl. Further metal oxide precursors comprise silicon tetrachloride and organically modified silica, for example, $CH_3Si(OCH_3)_3$, $PhSi(OCH_3)_3$, and $(CH_3)_2Si(OCH_3)_2$. Other metal oxide precursors to the network of metal oxide include metal silicates, for example, potassium silicate, sodium silicate, and lithium silicate. K, Na or Li ions can be removed using a DOWEX® cation exchange resin (sold by Dow Chemical, Midland, Mich.) which generates polysilicic acid which gels at slightly acid to basic pH. The use of "LUDOX®" colloidal silica (E. I. du Pont de Nemours and Company, Wilmington, Del.) and fumed silica ("CAB-O-SIL®" sold by Cabot Corporation of Boston, Mass.) which can be gelled by altering pH and adjusting the concentration in solution will also yield a metal oxide network in the microcomposite of the invention. A representative metal oxide precursor for alumina is $Al(OC_4H_9)_3$.

One process for the preparation of the microcomposite of the present invention comprises mixing a solution that comprises a perfluorinated ion-exchange polymer containing pendant metal cation exchanged sulfonate and/or metal cation exchanged carboxylate groups, wherein the metal cation may be ligand coordinated, and optionally pendant sulfonic acid groups and/or pendant carboxylic acid groups, at least one metal oxide precursor, and a common solvent. Thus, the PFIEP of the microcomposite can contain pendant metal groups which are partially or fully metal cation exchanged, wherein the metal cation may be ligand coordinated.

The common solvent can comprise water and a lower aliphatic alcohol such as methanol, 1-propanol, 2-propanol, mixed ethers, n-butanol or a mixture thereof. Thus, in some cases the water necessary for gel formation can be supplied by the water in the reaction solvent. Other polar solvents which may be suitable for the particular metal oxide precursor and perfluorinated ion-exchange polymer selected include acetonitrile, dimethyl formamide, dimethylsulfoxide, nitromethane, tetrahydrofuran, acetone, and the like. Toluene, alkanes and fluorocarbon-containing solvents can also be useful in some instances to solubilize the polymer.

Next, gelation of the mixture is initiated. Gelation may in some instances self-initiate, for example, when water is present in the common solvent. Gelation can be initiated via rapid drying, such as spray drying, of the solution comprising the PFIEP and the at least one metal oxide precursor to yield a dried microcomposite. In other instances, gelation must be initiated, which can be achieved in a number of ways depending on the initial mixture of the perfluorinated ion-exchange polymer, at least one metal oxide precursor and solvent selected. Gelation is dependent on a number of factors such as the amount of water present. Other factors affecting gelation include temperature, pressure, solvent type, concentrations, pH and the nature of any acid or base used. If adjustment of pH is utilized to initiate gelation, the pH can be changed in a number of ways, for example, by adding a base to the PFIEP solution, by adding the PFIEP solution to the base, or by adding the metal oxide precursor to the solution than adjusting the pH with the base. Gels can also be formed by acid catalyzed gelation. See Sol-Gel Science, Brinker, C. J. and Scherer, G. W., Academic Press, 1990.

The mixture is allowed sufficient time for gelation to occur. The time required for gelation can vary widely depending on factors such as acidity, temperature, and concentration. It can vary from practically instantaneous to several days. Gelation can be carried out at virtually any temperature at which the solvent is in liquid form. The reaction is typically carried out at room temperature. Pressure during gelation is not critical and may vary widely. Typically gelation is carried out at atmospheric pressure and can be carried out over a wide range of acidity and basicity.

After gelation, but before isolation, the gel, still in the presence of the solvent, may optionally be allowed to stand for a period of time. This is referred to as aging.

The gel is dried at room temperature or at elevated temperatures in an oven for a time sufficient to remove the solvent. Drying can be done under vacuum, or in air, or using an inert gas such as nitrogen.

The process may further comprise contacting the solution comprising the PFIEP and the at least one metal oxide precursor, the gel or the final microcomposite with an aqueous solution comprising at least one metal salt or a salt of a ligand coordinated metal, which will convert some or all of any PFIEP pendant sulfonic acid and/or carboxylic acid groups present to metal cation exchanged groups. In the case of a salt having a metal cation different from the metal cation on the PFIEP pendant group, the final microcomposite can, as a result, have PFIEP with one pendant group that has a metal cation that is different from the metal cation on another pendant group.

Another process for the preparation of the microcomposite of the present invention comprises contacting a porous microcomposite comprising a perfluorinated ion-exchange polymer containing pendant sulfonic acid and/or carboxylic acid groups entrapped within and highly dispersed throughout a network of metal oxide, wherein the weight percentage of perfluorinated ion-exchange polymer in the microcomposite is from about 0.1 to 90 percent, wherein the size of the pores in the microcomposite is about 0.5 nm to about 75 nm, and wherein the microcomposite optionally further comprise pores having a size in the range of about 75 nm to about 1000 nm, with an aqueous solution comprising at least one metal salt or a salt of a ligand coordinated metal. Thus, a porous microcomposite comprising a PFIEP with fully acidified pendant groups is first prepared prior to contact with the at least one metal salt or the salt of a ligand coordinated metal. The porous microcomposite comprising the PFIEP with fully acidified pendant groups can be prepared similarly to the process described above except the PFIEP used during the mixing step would have pendant sulfonic acid and/or carboxylic acid groups only. Alternatively, the porous microcomposite comprising PFIEP with fully acidified pendant groups can be prepared from any type of PFIEP, e.g. fully acidified, fully metal cation exchanged or partially metal cation exchanged pendant groups, wherein the metal cation may be ligand coordinated. In this alternative process for preparation of the porous microcomposite which comprises PFIEP with pendant sulfonic acid and/or carboxylic acid groups (fully acidified PFIEP pendant groups), after gelation, optional aging and removal of the solvent, the microcomposite is contacted with an acid followed by removal of any excess acid, for example, by washing with deionized water. Suitable acids comprise HCl, $H_2SO_4$ and nitric acid.

Following contact of the porous microcomposite comprising PFIEP containing pendant sulfonic acid and/or carboxylic acid pendant groups (fully acidified) with the at least one metal salt, the solvent is removed to yield a porous microcomposite which comprises a perfluorinated ion-exchange polymer containing pendant metal cation exchanged sulfonate and/or metal cation exchanged carboxylate groups, and optionally pendant sulfonic acid and/or carboxylic acid groups, entrapped within and highly dispersed throughout a network of metal oxide, wherein the weight percentage of perfluorinated ion-exchange polymer in the microcomposite is from about 0.1 to 90 percent, wherein the size of the pores in the microcomposite is about 0.5 nm to about 75 nm, and wherein the microcomposite optionally further comprises pores having a size in the range of about 75 nm to about 1000 nm. Removal of the solvent can be accomplished by filtering and washing with deionized water, followed by drying at room temperature or at elevated temperatures in an oven. Drying can be under vacuum, or in air, or using an inert gas such as nitrogen.

Optionally, the microcomposite of the present invention can be ground and passed through a screen, preferably a 10-mesh screen. Grinding generates smaller particles (and greater surface area) which are more readily re-acidified, if desired. Grinding is especially useful for microcomposites having a high weight percent of PFIEP.

A number of reaction variables, for example acidity, basicity, temperature, aging, method of drying and drying time of gels, have been found to affect the pore size and pore size distribution. Both higher pH and longer aging of gels (before solvent removal) lead to larger final pore size in the dried PFIEP/metal oxide gels. Pore size can be varied over a wide range (about 0.5 to about 75 nm) depending on the variables described above. Aging of the wet gels (in the presence of the solvent) for a few hours at about 75° C. also leads to an increase in pore size although over a smaller range. This effect is characteristic of silica type gels, where the aging effect gives rise to an increasingly cross linked network which upon drying is more resistant to shrinkage and thus a higher pore size results. See, for example, the text Sol-Gel Science, Brinker, C. J. and Scherer, G. W., Academic Press, 1990, pp. 518–523. In the present invention, preferred pore size is about 0.1 nm to about 75 nm, more preferred about 0.5 nm to about 50 nm, most preferred is about 0.5 to about 30 nm.

Microcomposites further comprising macropores (about 75 nm to about 1000 nm in size) have also been developed hereunder which have both high surface area and micro-, meso- and macroporosity. Such a structure is easily accessible for catalytic and ion exchange purposes. This unique microstructure of the present invention is prepared by adding about 1 to 80 wt % (based upon gel weight) of submicron size particles of an acid extractable filler particle to the PFIEP and metal oxide precursor solution prior to the gelation step. "Acid extractable filler particles" include particles which are insoluble in the preparative gel-forming solvent, but are acid soluble and extractable from the formed microcomposite. Such filler particles include, for example, alkali metal carbonates or alkaline earth carbonates, such as calcium carbonate, sodium carbonate and potassium carbonate. After gelation and removal of the solvent, the microcomposite is acidified whereupon the acid extractable filler particle dissolves out of the microcomposite leaving macro (about 75 nm to about 1000 nm) pores throughout the microcomposite with a sub-structure of micro and meso pores (about 0.5 nm to about 75 nm). This kind of structure offers a high surface area making the PFIEP and metal oxide network readily accessible throughout the microcomposite.

It is believed that the structure of the microcomposite of the present invention consists of a continuous metal oxide phase which entraps a highly dispersed PFIEP within and throughout its connected network. The porous nature of the microcomposite can be readily demonstrated, for example, by solvent absorption. The microcomposite can be observed to emit bubbles which are evolved due to the displacement of the air from within the porous microcomposite.

The distribution of the PFIEP entrapped within and throughout the metal oxide network is on a very fine sub-micron scale. The distribution can be investigated using electron microscopy, with energy dispersive X-ray analysis, which provides for the analysis of the elements Si and O (when using silica, for example) and C and F from the PFIEP. Fractured surfaces within a particle and several different particles for compositions ranging from 10 to 40 wt % "NAFION®" PFIEP were analyzed, and all of the regions investigated showed the presence of both the silica and PFIEP from the edge to the center of the microcomposite particles; thus the microcomposite exhibited an intimate mixture of Si and F. No areas enriched in entirely Si or entirely F were observed, rather a uniform distribution of Si and F was seen. This bicomponent description is believed to be accurate for areas as low 0.1 micrometer in size. The morphology of the microcomposites, as prepared by Experiment 1, is somewhat particulate in nature, again as observed using scanning electron microscopy. This is typical of silica gel type material prepared using a sol-gel procedure. The primary particle size within such a microcomposite sample is on the order of 5–10 nm. This was also confirmed using small angle x-ray scattering experiments on the material, which again revealed domain size in the range of 5–10 nm. The data is consistent with the PFIEP being entrapped within and highly dispersed throughout the silica.

Microcomposites of the present invention comprising PFIEP containing pendant metal cation exchanged sulfonate groups and/or pendant metal cation exchanged carboxylate groups, and sulfonic acid and/or carboyxlic acid groups (partially metal cation exchanged) are useful as ion exchange resins, and as catalysts, for example, for alkylating aliphatic or aromatic hydrocarbons, for decomposing organic hydroperoxides, such as cumene hydroperoxide, for sulfonating or nitrating organic compounds, and for oxyalkylating hydroxylic compounds. Other applications for microcomposite comprising PFIEP containing pendant metal cation exchanged sulfonate groups and/or pendant carboxylate groups, and sulfonic acid and/or carboyxlic acid groups (partially metal cation exchanged) comprise hydrocarbon isomerizations and polymerization; carbonylation and carboxylation reactions; hydrolysis and condensation reactions, esterifications and etherification; hydrations and oxidations; aromatic acylation, alkylation and nitration; and isomerization and metathesis reactions.

Microcomposites of the present invention comprising PFIEP containing pendant metal cation exchanged sulfonate and/or metal cation exchanged carboxylate groups, and optionally pendant sulfonic acid and/or carboxylic acid groups (fully or partially metal cation exchanged) are useful as catalysts in the isomerization of 1,4-dichlorobutene-2 to 3,4-dichlorobutene-1. This process comprises contacting 1,4-dichlorobutene-2 with a catalytic amount of a porous microcomposite which comprises a perfluorinated ion-exchange polymer containing metal cation exchanged pendant sulfonate and/or metal cation exchanged carboxylate groups, wherein the metal cation may be ligand coordinated, and optionally pendant sulfonic acid and/or carboxylic acid groups, entrapped within and highly dispersed throughout a network of metal oxide, wherein the weight percentage of perfluorinated ion-exchange polymer in the microcomposite is from about 0.1 to 90 percent, wherein the size of the pores in the microconiposite is about 0.5 nm to about 75 nm, and wherein the microcomposite optionally further comprises pores having a size in the range of about 75 nm to about 1000 nm, in a common solvent, or neat without solvent, under an inert atmosphere at a temperature ranging from about 80° C. to about 180° C.; and recovering the 3,4-dichlorobutene-1. The process can be carried out in the liquid phase with a solvent such as decane, or neat without solvent, under ambient pressure. The amount of 1,4-dichlorobutene-2 to microcomposite is preferably 1–50:1.

Preferably, the PFIEP of the microcomposite used in the above dichlorobutene isomerization contains pendant metal cation exchanged sulfonate and sulfonic acid groups. The weight percent of perfluorinated ion-exchange polymer is preferably about 5% to about 25%. A most preferred perfluorinated ion-exchange polymer is a "NAFION®" PFIEP prepared from resin comprising tetrafluoroethylene and perfluoro(3,6-dioxa-4-methyl-7-octenesulfonyl fluoride). The preferred metal oxide is silica, and the preferred metal cation is selected from the group consisting of cations of Cr, Sn, Al, Fe, Os, Co, Zn, Hg, Li, Na, Cu, Pd, and Ru; most preferably the metal cation is selected from the group consisting of cations of Cu and Pd.

In addition to the uses described above, the microcomposites of the present invention are useful in the area of electrochemistry and electrochromics. The advantage of the present microcomposites over catalysts previously used in these areas is their high surface area and rapid diffusion. A free flowing solution comprising PFIEP and at least one metal oxide precursor prepared as described above can be applied as a coating to an electrode surface via, for example, dipping or spin coating. After gelation of the solution, the solvent can be left to evaporate to yield an electrode having a coating comprising the porous microcomposite of the present invention. The PFIEP pendant groups of the dried, porous microcomposite coating can optionally be acidified and then exchanged with metal cation or with other electrochemically active organic cation species by contacting the coating with a solution comprising a metal salt, a solution comprising a salt of a ligand coordinated metal, such as $Ru(bipyridyl)_3Cl_2$, or a solution which comprises an electrochemically active organic cation molecule, such as methyl viologen. Alternatively, the solution comprising PFIEP and the metal oxide precursor can further comprise a solution which comprises a metal salt, a solution which comprises a salt of a ligand coordinated metal, or a solution which comprises an electrochemically active organic cation molecule. Representative and preferred examples of electrochemically active organic cation molecules are alkyl viologen, e.g. methyl viologen, and aryl viologen, e.g. benzyl viologen. The electrode coating is useful in electrode material or as an electrocatalyst.

The present invention further provides an electrochromic material, comprising: a porous microcomposite which comprises a perfluorinated ion-exchange polymer containing pendant metal cation exchanged sulfonate and/or metal cation exchanged carboxylate groups, wherein the metal cation may be ligand coordinated, or pendant electrochemically active organic cation sulfonate and/or electrochemically active organic cation carboxylate groups, and optionally pendant sulfonic acid and/or carboxylic acid groups, entrapped within and highly dispersed throughout a network of metal oxide, wherein the weight percentage of perfluorinated ion-exchange polymer in the microcomposite is from about 0.1 to about 90 percent, wherein the size of the pores in the microcomposite is about 0.5 nm to about 75 nm, and wherein the microcomposite optionally further comprises pores having a size in the range of about 75 nm to about 1000 nm. The porous micrcomposite of this electrochromic material is prepared as described above for the electrode coating.

For some of the catalytic applications described above, some brown coloration may form upon the microcomposite. Microcomposites of the present invention can be regenerated by treatment with an acid, for example nitric acid, followed by contact with a solution comprising the desired metal salt, the salt of a ligand coordinated metal, or electrochemically active organic cation molecule. The microcomposite is contacted with the acid and then stirred at a temperature ranging from about 15° C. to about 100° C. for about 1 hr to about 26 hrs. Subsequent washing with de-ionized water can be used to remove excess acid. The microcomposite is then dried at a temperature ranging from about 100° C. to about 200° C., preferably under vacuum for about 1 hr to about 60 hrs whereupon it is contacted with an aqueous solution of the metal salt, the salt of a ligand coordinated metal, or the electrochemically active organic cation molecule, to yield amicrocomposite of the present invention.

EXAMPLES

"NAFION®" PFIEP solutions can be purchased from Aldrich Chemical Co., Milwaukee, Wis., or PFIEP solutions generally can be prepared using the procedure of U.S. Pat. No. 5,094,995 and U.S. Pat. No. 4,433,082. The "NAFION®" PFIEP solution referred to in the examples below is, unless otherwise noted, "NAFION®" NR 005, a "NAFION®" solution available from DuPont Nafion® Products, Fayetteville, N.C., and also known as "NAFION®" SE-5110, and is prepared from resin which is approximately 6.3 (TFE) molecules for every perfluoro(3,6-dioxa-4-methyl-7-octenesulfonyl fluoride) molecule ($CF_2=CF-O-[CF_2CF(CF)]-O-CF_2CF_2-SO_2F$ (PSEPVE)) and has an equivalent weight of approximately 1070. "NAFION®" NR50 PFIEP, the same resin used to prepared the NR005 (SE-5110) solution is available in pellet form from E. I. du Pont de Nemours and Company, Wilmington, Del. (distributed by Aldrich Chemical Company). "NAFION®" NR55 PFIEP is similarly available and structured with carboxylic ends as well as sulfonated ends on the pendant groups.

Experiment 1

Preparation of a 40 wt % PFIEP/60 wt % Silica Microcomposite

To 200 mL of a "NAFION®" perfluorinated resin solution (which consisted of 5 wt % "NAFION®" PFIEP in a mixture of lower alcohols and water) was added 25 g of a 0.4 M NaOH and the solution was stirred. Separately, in another beaker, to 34 g of tetramethoxysilane was added 5.44 g of distilled water and 0.5 g of 0.04 M HCl and the solution rapidly stirred for 10 minutes. After 10 minutes the silicon containing solution was added to the rapidly stirring "NAFION®" solution and stirring was continued for about 10 seconds to ensure good mixing. The solution was left to stand. It was observed that the whole solution formed a gel within a few seconds. The gel was covered and left to stand for 4 hours after which time the cover was removed and the gel was placed in an oven at 90° C. with a slow stream of nitrogen flushing through the oven. The gel was left to dry for 15 hours. The resultant dry-glass-like pieces were then further dried at 140° C. under vacuum for 15 hours. The resultant material was re-acidified with HCl as follows to convert the perfluorosulfonic acid into the acidic form. The dried material was placed in 100 mL of 3.5 M HCl and the mixture stirred for 1 hour. The HCl solution was removed via filtration and the solid resuspended in 100 mL of 3.5 M HCl and stirred for a further hour. The filtering and acidification step was repeated a total of five times. Finally, the solid was placed in distilled deionized water (200 mL) and stirred for 1 hour, filtered and resuspended in water (200 mL) and stirred in order to remove the excess HCl. The solid was filtered and dried at 140° C. for 24 hours. The yield was about 22 g. The final material was a finely particulate glass-like material with a light yellow coloration. The content of the PFIEP was about 40 wt %. The solid had a hard texture typical of sol-gel derived silica type materials with some pieces up to a few mm in size. The material was highly porous with a surface are of 200 $m^2$ per gram (BET surface area), a single point pore volume of 0.38 cc/g and an average pore diameter of 5.59 nm.

Experiment 2

Preparation of 40 wt % PFIEP/60 wt % Silica Microcomposite with Dual Porosity having Both Macro (ca. 500 nm) and Micro (ca. 2–15 nm) Pores To 100 mL of the "NAFION®" solution (which consisted of 5 wt % "NAFION®" PFIEP in a mixture of lower alcohols and water) was added 15 g of a 0.4 M NaOH and the solution stirred. 4 g of calcium carbonate (Albafil Specialty Minerals, Adams, Mass.) with a particle size of about 0.5 microns was added to the basic PFIEP and calcium carbonate mixture which was ultrasonicated for 1 minute to 10 minutes using a sonic probe (Heat Systems Inc., Farmingdale, N.Y.). Separately in another beaker, 1.7 g of distilled water and 0.25 g of 0.04 M HCl was added to 17 g of tetramethoxysilane and the solution rapidly stirred for 10 minutes. After 10 minutes the silicon containing solution was added to the rapidly stirring PFIEP solution and stirring was continued for about 10 seconds to ensure good mixing. The solution was left to stand; it was observed that the whole solution formed a gel within a few seconds. The gel was covered and left to stand for 4 hours after which point the cover was removed and the gel was placed in an oven at 90° C. with a slow stream of nitrogen flushing through the oven. The gel was left to dry for 15 hours. The resultant dry glass-like pieces were then further dried at 140° C. under house vacuum for 15 hours. The resultant material was reacidified with HCl as follows to convert the perfluorosulfonic acid into the acidic form and to dissolve out the calcium carbonate. The dried material was placed in 100 mL of 3.5 M HCl and the mixture stirred for 1 hour. Upon addition of the acid a large amount of gas was evolved (due to the reaction of the acid with HCl). The HCl solution was removed via filtration and the solid resuspended in 100 mL of 3.5 M HCl and stirred for a further hour. The filtering and acidification step was repeated a total of five times. Finally the solid was placed in distilled deionized water (200 mL) and stirred for 1 hour, filtered and resuspended in water (200 mL) and stirred in order to remove the excess HCl. The solid was filtered and dried at 125° C. for 24 hours. The final material was a glass-like material with a light yellow coloration. The microstructure of the derived material was investigated using scanning electron microscopy. The micrograph clearly showed very large pores about 0.5–1 micron in size. Using energy dispersive x-ray analysis, no Ca could be detected showing that most of the calcium carbonate had been removed upon reacidification. The material was highly porous with a surface area of 310 $m^2/g$ (BET surface area), and a single point pore volume of 0.46 cc/g.

Experiment 3

Microcomposite of "NAFION®" (NR55) PFIEP in Silica 150 mL of a 5% solution of "NAFION®" NR55 (which contained both sulfonic acid and carboxylic acid groups) was added to 60 mL of isopropanol, 15 mL of methanol, and 75 mL of water. To this was added 150 g of 0.4 M NaOH. Separately, 204 g of TMOS, 32.6 g of water and 3 g of 0.04 M HCl was stirred for 20 mins and then added to the PFIEP solution. The gel that formed was dried at 100° C. over 24 hours, ground and passed through a 10-mesh screen. The material was then stirred with 3.5 M HCl for 1 hour (with 500 mL of acid), followed by washing with 500 ml of de-ionized water. The solid was collected by filtration. Acidification, washing and filtration were repeated at total of 5 times and after the final wash the solid was dried under vacuum at 100° C. for 24 hours. Yield of dried product was 92.6 g. The PFIEP content was 7.5 wt %.

Experiment 4

PFIEP/Si—Al—Zr Microcomposite 20.4 g of tetramethoxysilane, 3.6 g of water and 0.3 g of 0.04 M HCl was stirrred for 20 mins. and added to 5 g of the mixed aluminum/zirconium complex $(Al_2Zr(OR)_x$ (available from Gelest, Tullytown, Pa.). The mixture was stirred for 5 mins. 30 g of a 5% "NAFION®" solution and 15 g of 0.4 M NaOH were mixed and added to the Si—Al—Zr containing solution, and the material was placed in an over at 75° C. and dried at 100° C.

Experiment 5

13.5 wt % PFIEP/Silica Microcomposite with Pore Diameter ca. 10 nm 204 g of tetramethoxysilane, 33 g of distilled water and 3 g of 0.04 M HCl was stirred for 45 mins. to give a clear solution. To 300 mL of a "NAFION®" solution (which contained 5% of "NAFION®" PFIEP by weight) was added 150 mL of a 0.4 M NaOH solution, while the PFIEP solution was being stirred After addition of the sodium hydroxide solution the resulting solution was stirred for a further 15 min. The silicon containing solution was added rapidly to the stirred PFIEP containing solution. After about 10–15 seconds the solution gelled to a solid mass. The gel was placed in an oven and dried at a temperature of about 95° C., over a period of about 2 days, followed by drying under vacuum overnight. The hard glass-like product was ground and passed through a 10-mesh screen. The material was then stirred with 3.5 M HCl for hour with 500 mL of acid, followed by washing with 500 mL of deionized water. The solid was collected by filtration. Acidification, washing and filtration were repeated a total of 5 times and after the final wash the solid was dried under vacuum at 100° C. for 24 hours. Yield of dried product was 98 g. The surface area (determined by BET), pore volume and pore diameter was determined to be 344 $m^2/g$, 0.85 cc/g and 9.8 nm, respectively.

Example 1

$Cu^{2+}$/PFIEP/Silica Microcomposite 0.58 g $CuSO_4 \cdot 5H_2O$ and 20 g of a "NAFION®" PFIEP/silica microcomposite, wherein the weight percent of the PFIEP was 13%, prepared similarly to the microcomposite of Experiment 5, was added to an aqueous solution and stirred at room temperature for 4 hrs. The microcomposite was filtered and washed extensively with distilled water to remove the excess metal salt. The final microcomposites were dried in a vacuum oven at 110° C. for over night.

Example 2

$Pd^{2+}$/PFIEP/Silica Microcomposite 0.53 g $Pd(NO_3)_2 \cdot xH_2O$ and 20 g of a "NAFION®" PFIEP/silica microcomposite, wherein the weight percent of the PFIEP was 13%, prepared similarly to the microcomposite of Experiment 5, was added to an aqueous solution and stirred at room temperature for 4 hrs. The microcomposite was filtered and washed extensively with distilled water to remove the excess metal salt. The final microcomposites were dried in a vacuum oven at 110° C. for over night.

Example 3

$Al^{3+}$/PFIEP/Silica Microcomposite 0.87 g $Al(NO_3)_3 \cdot 9H_2O$ and 20 g of a "NAFION®" PFIEP/silica microcomposite, wherein the weight percent of the PFIEP was 13%, prepared similarly to the microcomposite of Experiment 5, was added to an aqueous solution and stirred at room temperature for 4 hrs. The microcomposite was filtered and washed extensively with distilled water to remove the excess metal salt. The final microcomposites were dried in a vacuum oven at 110° C. for over night.

Example 4

$Fe^{3+}$/PFIEP/Silica Microcomposite 3.8 g $FeCl_3$ and 10 g of a "NAFION®" PFIEP/silica microcomposite, wherein the weight percent of the PFIEP was 13%, prepared similarly to the microcomposite of Experiment 5, was added to an aqueous solution and stirred at room temperature for 4 hrs. The microcomposite was filtered and washed extensively with distilled water to remove the excess metal salt. The final microcomposites were dried in a vacuum oven at 110° C. for over night.

Example 5

$Sn^{2+}$/PFIEP/Silica Microcomposite 0.52 g $SnCl_2 \cdot 2H_2O$ and 20 g of a "NAFION®" PFIEP/silica microcomposite, wherein the weight percent of the PFIEP was 13%, prepared similarly to the microcomposite of Experiment 5, was added to an aqueous solution and stirred at room temperature for 4 hrs. The microcomposite was filtered and washed extensively with distilled water to remove the excess metal salt. The final microcomposites were dried in a vacuum oven at 110° C. for over night.

Example 6

$Cr^{3+}$/PFIEP/Silica Microcomposite 0.93 g $Cr(NO_3)_3 \cdot 9H_2O$ and 20 g of a "NAFION®" PFIEP/silica microcomposite, wherein the weight percent of the PFIEP was 13%, prepared similarly to the microcomposite of Experiment 5, was added to an aqueous solution and stirred at room temperature for 4 hrs. The microcomposite was filtered and washed extensively with distilled water to remove the excess metal salt. The final microcomposites were dried in a vacuum oven at 110° C. for over night.

Comparative Example A $Cu^{2+}$/PFIEP Catalyst 4.46 g $CuSO_4 \cdot 5 H_2O$ and 20 g NAFION PFIEP NR50 resin was added to an aqueous solution and stirred at room temperature for 4 hrs. The resin was filtered and washed extensively with distilled water to remove the excess metal salt. The final catalysts were dried in a vacuum oven at 110° C. for over night.

Example 7

Catalytic Testing for Isomerization of 1,4-dichlorobutene-2 to 3,4-dichlorobutene-1

Prior to testing, each catalyst was dried at 150° C. under vacuum overnight. For each test, 0.5 g catalyst, 2.0 g of the reactant 1,4-dichlorobutene-2 and 50 g solvent decane were added to a glass reactor, a three neck flask which was attached to a condenser. The isomerization reaction was carried out under ambient pressure at 130° C., under a nitrogen environment and agitated with a magnetic stir bar. The reaction mixture was sampled at certain time intervals and conversion of the reactant and product yields were determined by gas chromatography (GC) analysis of those samples. No by-product was detected in a significant amount.

Four catalysts were tested for the 1,4-dichlorobutene-2 isomerization to 3,4 dichlorobutene and the 3,4-dichlorobutene-1 yields after 1 hour of reaction time were listed in Table 1. The four catalysts were: a $Cu^{2+}$/13 weight % "NAFION®" PFIEP/Silica microcomposite (as prepared in Example 1), a $Pd^{2+}$/13 weight % "NAFION®" PFIEP/Silica microcomposite (as prepared in Example 2), a 13 weight % "NAFION®" PFIEP/Silica microcomposite (prepared similarly to Experiment 5), and a $Cu^{2+}$/"NAFION®" NR50 PFIEP (as prepared in Comparative Example A).

TABLE 1

| Catalyst | 3.4-dichlorobutene-1 yield (mol %) |
|---|---|
| $Cu^{2+}$/13% PFIEP/Silica | 3.81 |
| $Pd^{2+}$/13% PFIEP/Silica | 3.15 |
| 13% PFIEP/Silica | 0.28 |
| $Cu^{2+}$/"NAFION ®" NR50 | 0.04 |

Example 8

Ru complex/PFIEP/Silica Microcomposite 0.1 g of rutheniumtrisbipyridylchloride (Ru(bipyridyl)$_3Cl_2$) was added to 10 g of deionized water. To this 1 g of a "NAFION®" PFIEP/silica microcomposite, wherein the weight percent of the PFIEP was 13%, prepared similarly to the microcomposite of Experiment 5, and the mixture was left overnight. The pH of the solution became more acidic and was measured at 2.3 which showed that the acid ($H^+$) ions were being replaced by the cationic complex (Ru(bipyridyl)$_3^{+2}$). The solid was washed with water and dried in vacuum at 100° C. yielding a bright red solid.

What is claimed is:

1. A process for the isomerization of 1,4-dichlorobutene-2 to 3,4-dichlorobutene-1, comprising: contacting 1,4-dichlorobutene-2 with a catalytic amount of a porous microcomposite which comprises a perfluorinated ion-exchange polymer containing pendant metal cation exchanged sulfonate groups, metal cation exchanged carboxylate groups, or metal cation exchanged sulfonate and carboxylate groups, wherein the metal cation may be ligand coordinated, and optionally pendant sulfonic acid groups, carboxylic acid groups, or sulfonic acid and carboxylic acid groups, entrapped within and highly dispersed throughout a network of metal oxide, a network of silica, or a network of metal oxide and silica, wherein the weight percentage of perfluorinated ion-exchange polymer in the microcomposite is from about 0.1 to about 90 percent, wherein the size of a first set of pores in the microcomposite is about 0.5 nm to about 75 nm, and wherein the microcomposite optionally further comprises a second set of pores having a size in the range of about 75 nm to about 1000 nm, in a solvent, or without solvent, under an inert atmosphere at a temperature ranging from about 80° C. to about 180° C.; and recovering the 3,4-dichlorobutene-1.

2. The process of claim 1 wherein the perfluorinated ion-exchange polymer contains pendant metal cation exchanged sulfonate groups, and optionally pendant sulfonic acid groups, wherein the metal cation may be ligand coordinated, and wherein the metal cation exchanged sulfonate groups constitute from 1 to 100% of the total sulfonate plus sulfonic acid groups present, and wherein the network is silica.

3. The process of claim 1 wherein the metal cation is selected from the group consisting of cations of: Cu and Pd.

* * * * *